United States Patent
Weissman

(10) Patent No.: US 11,358,915 B2
(45) Date of Patent: Jun. 14, 2022

(54) PROCESS FOR CONVERTING ALKANES TO OLEFINS

(71) Applicant: PRECISION COMBUSTION, INC., North Haven, CT (US)

(72) Inventor: Jeffrey Weissman, Guilford, CT (US)

(73) Assignee: PRECISION COMBUSTION, INC., North Haven, CT (US)

( * ) Notice: Subject to any disclaimer, the term of this patent is extended or adjusted under 35 U.S.C. 154(b) by 0 days.

(21) Appl. No.: 17/318,689

(22) Filed: May 12, 2021

(65) Prior Publication Data

US 2021/0261480 A1 Aug. 26, 2021

Related U.S. Application Data

(62) Division of application No. 16/273,234, filed on Feb. 12, 2019, now Pat. No. 11,040,928.

(Continued)

(51) Int. Cl.
*C07C 2/84* (2006.01)
*C07C 5/333* (2006.01)
(Continued)

(52) U.S. Cl.
CPC ............ *C07C 2/84* (2013.01); *B01J 12/007* (2013.01); *B01J 19/249* (2013.01);
(Continued)

(58) Field of Classification Search
CPC . C07C 2/84; C07C 5/333; C07C 11/04; B01J 12/007; B01J 19/2415; B01J 19/249;
(Continued)

(56) References Cited

U.S. PATENT DOCUMENTS

| 4,455,236 A | 6/1984 | Kim |
| 5,266,281 A | 11/1993 | Kao |

(Continued)

FOREIGN PATENT DOCUMENTS

| DE | 102012016561 A1 | 2/2014 |
| EP | 0962422 A1 | 12/1999 |
| EP | 2045212 A1 | 4/2009 |

OTHER PUBLICATIONS

Ketang Liu, et al., "Oxidative coupling of methane in solid oxide fuel cell tubular membrane reactor with high ethylene yield," Catalysis Communications, 96 (2017), 23-27.

(Continued)

*Primary Examiner* — Thuan D Dang
(74) *Attorney, Agent, or Firm* — Marie Zuckerman; Andrew D. Gathy

(57) ABSTRACT

A process and apparatus for converting an alkane to an olefin. In one embodiment, the process involves oxidative coupling of an alkane, e.g., methane, with an oxidant, such as air, to produce an olefin having twice the number of carbon atoms as the alkane, e.g., ethylene. In another embodiment, the process involves oxidative dehydrogenation of an alkane, e.g., ethane, with an oxidant to form an olefin having the same number of carbon atoms as the alkane, e.g., ethylene. The process involves passing a flow of the oxidant from a first flow passage through a porous medium; diffusing a flow of the alkane from a second flow passage into the porous medium; and contacting the reactant alkane and the oxidant in the presence of a catalyst within the porous medium to produce the olefin.

13 Claims, 8 Drawing Sheets

Related U.S. Application Data

(60) Provisional application No. 62/661,223, filed on Apr. 23, 2018.

(51) Int. Cl.
  *B01J 12/00* (2006.01)
  *B01J 19/24* (2006.01)
  *C07C 11/04* (2006.01)

(52) U.S. Cl.
  CPC .......... *B01J 19/2415* (2013.01); *C07C 5/333* (2013.01); *B01J 2219/247* (2013.01); *B01J 2219/2409* (2013.01); *B01J 2219/2458* (2013.01); *C07C 11/04* (2013.01)

(58) Field of Classification Search
  CPC .............. B01J 8/0257; B01J 2219/2409; B01J 2219/2458; B01J 2219/247; B01J 2208/00194; B01J 8/0285; B01J 8/0465; B01J 8/0496; B01J 8/067
  See application file for complete search history.

(56) References Cited

U.S. PATENT DOCUMENTS

| | | | |
|---|---|---|---|
| 5,583,240 | A | 12/1996 | Asher |
| 6,838,064 | B2 | 1/2005 | Sakai |
| 6,977,064 | B1 | 12/2005 | Adris |
| 7,399,414 | B2 | 7/2008 | Raeder |
| 7,547,334 | B2 | 6/2009 | Brundage |
| 7,550,643 | B2 | 6/2009 | Pfefferle |
| 7,550,644 | B2 | 6/2009 | Pfefferle |
| 9,433,913 | B2 | 9/2016 | Pfefferle |
| 9,561,958 | B2 | 2/2017 | Quintero |
| 10,076,739 | B1 | 9/2018 | Weissman |
| 2012/0258037 | A1 | 10/2012 | Pham |
| 2014/0107233 | A1 | 4/2014 | Banister |
| 2014/0249339 | A1 | 9/2014 | Simanzhenkov |

OTHER PUBLICATIONS

Canan Karakaya and Robert J. Kee, "Progress in the direct catalytic conversion of methane to fuels and chemicals," Progress in Energy and Combustion Science, 55 (2016), 60-97.

H. R. Godini, et al., "Experimental and model-based analysis of membrane reactor performance for methane oxidative coupling: Effect of radial heat and mass transfer," Journal of Industrial and Engineering Chemistry, 20 (2014), 1993-2002.

Edrick Morales & Jack Lunsford, "Oxidative Dehydrogenation of Ethane Over a Lithium-Promoted Magnesium Oxide Catalyst," Journal of Catalysis, 118, 255-265 (1989).

PROCESS FOR CONVERTING ALKANES TO OLEFINS

CROSS-REFERENCE TO RELATED APPLICATIONS

This application is a divisional of U.S. nonprovisional application Ser. No. 16/273,234, filed Feb. 12, 2019, now allowed, which claims benefit of U.S. provisional application No. 62/661,223, filed Apr. 23, 2018; the foregoing applications being incorporated herein by reference.

GOVERNMENT RIGHTS

This invention was made with support from the U.S. government under Contract No. DE-SC0011353, sponsored by the Department of Energy. The U.S. Government holds certain rights in this invention.

FIELD OF THE INVENTION

This invention pertains to a process of converting a reactant alkane to form a product olefin (alkene). This invention embraces oxidative coupling wherein a reactant alkane is converted into an olefin having a greater number of carbon atoms as compared to the reactant alkane. Such a process is exemplified by the oxidative coupling of methane, a C1 alkane, in the presence of an oxidant, such as oxygen or air, to form ethylene, a C2 alkene. This invention also embraces oxidative dehydrogenation wherein a reactant alkane is converted to an olefin having the same number of carbon atoms as the reactant alkane. Such a process is exemplified by the oxidative dehydrogenation of a C2 alkane, such as ethane, in the presence of an oxidant, such as oxygen or air, to form a C2 olefin, such as ethylene. Olefins find widespread use as starting materials in the manufacture of plastics via polymerization reactions, in the manufacture of alcohols and ketones via hydroformylation processes, and in the manufacture of fuels via oligomerization processes.

BACKGROUND OF THE INVENTION

The direct conversion of an alkane with an oxidant to an olefin is hampered by several undesirable side reactions that are difficult to control. The problem can be illustrated with methane and its direct oxidative coupling to ethylene. In the desired process, methane and oxygen are reacted in the presence of an oxidative coupling catalyst to form ethylene and water as a byproduct, as shown in Equation 1:

$$2CH_4 + O_2 \rightarrow C_2H_4 + 2H_2O \quad \text{(Eqn. 1)}$$

In one side reaction, methane can be partially oxidized (reformed) in the presence of the catalyst to form carbon monoxide and hydrogen (synthesis gas), as shown in Equation 2:

$$CH_4 + \tfrac{1}{2}O_2 \rightarrow CO + 2H_2 \quad \text{(Eqn. 2)}$$

Likewise, methane and oxygen in the presence or absence of catalyst can be combusted to complete oxidation products, as shown in Equation 3:

$$CH_4 + 2O_2 \rightarrow CO_2 + 2H_2O \quad \text{(Eqn. 3)}$$

In yet another side reaction, in the presence of hydrogen the ethylene product can be catalytically hydrogenated or homogeneously reacted in a gas-phase to ethane, as shown in Equation 4:

$$C_2H_4 + H_2 \rightarrow C_2H_6 \quad \text{(Eqn. 4)}$$

High methane to oxygen molar ratios, for example, greater than 5:1 ($CH_4/O_2 > 5:1$), favor selectivity to ethylene, but at a cost of low methane conversion; while molar ratios close to stoichiometric ($CH_4/O_2 = 2:1$, as per Eqn. 1) favor reforming and combustion processes at a cost of low ethylene selectivity. To date, this behavior has limited catalyst utilization and ethylene productivity on a weight-hourly space velocity basis to unacceptably low values. The undesirable side reactions and outcomes observed for methane conversion to ethylene are generalizable to the conversion of high carbon alkanes having more than one carbon atom to related higher carbon olefins.

Prior attempts have been made to use porous flow control elements or membranes or other means to distribute oxygen through a tubular or annular reactor to reduce the aforementioned undesirable side reactions that reduce the production of olefin. See, for example, U.S. Pat. No. 9,433,913, as well as Kefeng Liu, et al., "Oxidative coupling of methane in solid oxide fuel cell tubular membrane reactor with high ethylene yield," Catalysis Communications, 96 (2017), pp. 23-27; and H. R. Godini, et al., "Experimental and model-based analysis of membrane reactor performance for methane oxidative coupling: Effect of radial heat and mass transfer," J. Industrial Engineering Chemistry, 20 (2014), pp. 1993-2002. Unfortunately, these attempts continue to result in low productivity of olefin, because relative rates of methane and oxygen utilization remain locally uncontrolled, which then leads to over-reaction as noted hereinabove, unacceptably low weight-based utilization of methane, and unacceptably low catalyst-based productivity to olefinic products.

In view of the above, it would be desirable to discover a novel and improved process of converting an alkane in the presence of an oxidant to an olefin, either through an oxidative coupling or oxidative dehydrogenation process. Such a process should provide greater local control over rates of alkane and oxygen utilization, which should then provide for less over-reaction to undesirable side-products, an acceptable weight-based utilization of alkane, and an acceptable catalyst-based productivity to olefinic products.

SUMMARY OF THE INVENTION

In one aspect, this invention provides for a process of converting an alkane to an olefin, comprising:
(a) passing a flow of an oxidant through a first inlet into a first chamber defining a first flow passage;
(b) passing a flow of an alkane through a second inlet into a second chamber defining a second flow passage, wherein a porous medium having an oxidative coupling or dehydrogenation catalyst supported therein separates the first flow passage from the second flow passage;
(c) applying a pressure in the first flow passage sufficient to provide a bulk flux of the oxidant through the porous medium into the second chamber;
(d) adjusting the flow of the alkane such that a ratio of diffusive flux of the alkane into the porous medium to the bulk flux of the oxidant through the porous medium is greater than 1:1;
(e) contacting the oxidant and the alkane at the catalyst within the porous medium under reaction conditions sufficient to produce the olefin, which thereafter flows into the second flow passage and exits through an outlet in the second chamber.

In another aspect, this invention provides for a chemical reactor comprising:
(a) a first chamber comprising a first inlet and a first flow passage;
(b) a second chamber comprising a second inlet and a second flow passage;
(c) a porous medium having an oxidative coupling or dehydrogenation catalyst supported therein, the porous medium separating the first flow passage from the second flow passage;
(d) an outlet from the second chamber.

The process of this invention, which employs a specific chemical reactor apparatus and specific process features, advantageously provides for an improved conversion of alkane and improved selectivity to and production of olefin products, as compared with prior art processes. As added advantages, the process of this invention provides for an improved productivity of olefin products, defined as weight of olefin products produced per weight of catalyst per unit time (e.g., g olefin/g-cat/hr), even at elevated inlet flow rates of alkane where conversion might be expected to decrease.

DRAWINGS

DETAILED DESCRIPTION OF THE INVENTION

Figure 1:
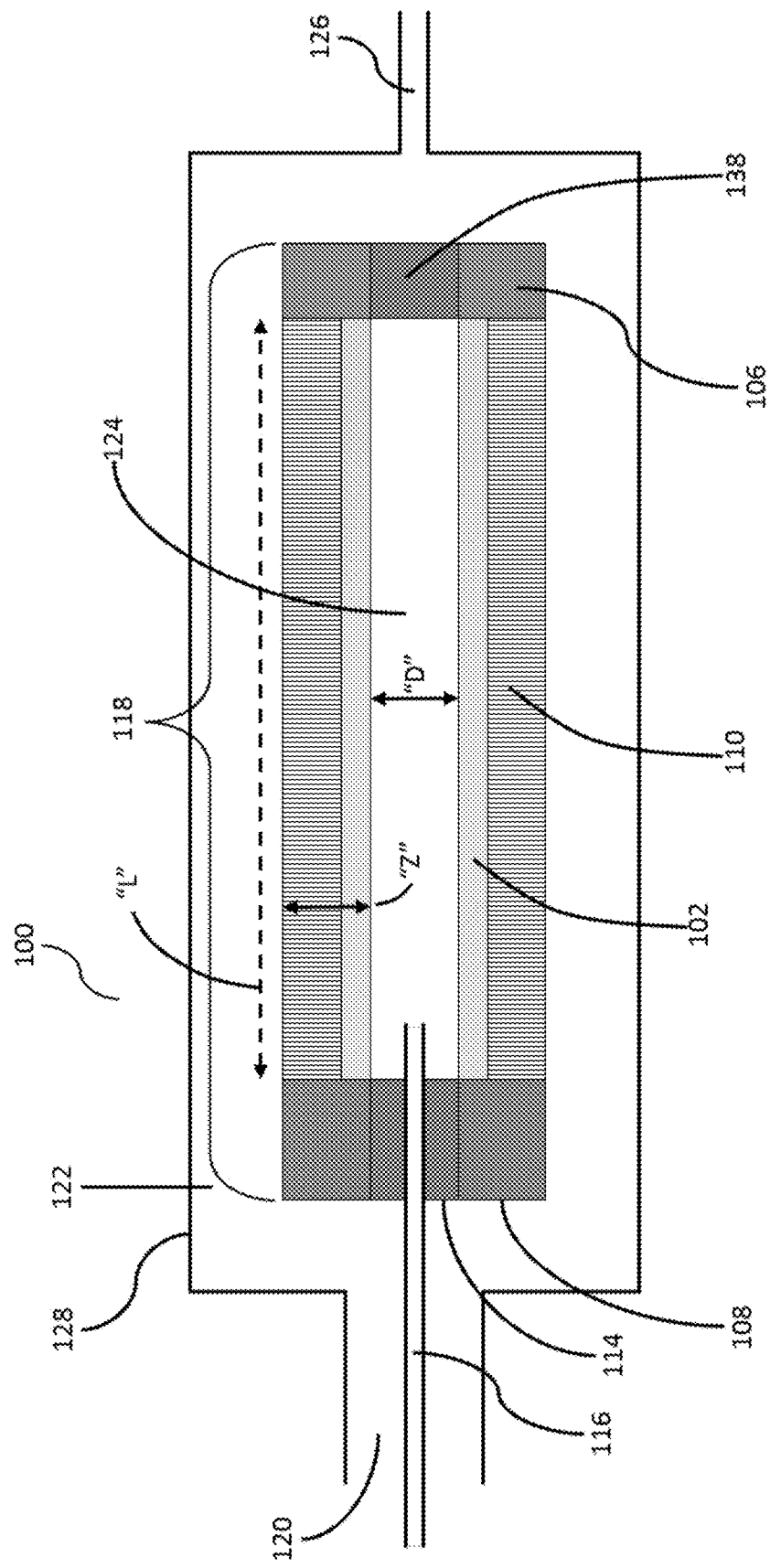
FIG. 1 depicts an exemplary embodiment of the process and a single tubular reactor apparatus of this invention.

In one embodiment, this invention provides for a process of oxidative coupling of a C1-4 alkane to form a C2-8 olefin having twice the number of carbon atoms as the C1-4 alkane, comprising:
(a) passing a flow of an oxidant through a first inlet into a first chamber defining a first flow passage;
(b) passing a flow of the C1-4 alkane through a second inlet into a second chamber defining a second flow passage, wherein a porous medium having an oxidative coupling catalyst supported therein separates the first flow passage from the second flow passage;
(c) applying a pressure in the first flow passage sufficient to provide a bulk flux of the oxidant through the porous medium into the second chamber;
(d) adjusting the flow of the C1-4 alkane such that a ratio of diffusive flux of the C1-4 alkane into the porous medium to the bulk flux of the oxidant through the porous medium is greater than 1:1;
(e) contacting the oxidant and the C1-4 alkane at the catalyst within the porous medium under reaction conditions sufficient to produce the C2-8 olefin having twice the number of carbon atoms as the C1-4 alkane, which thereafter flows into the second flow passage and exits through an outlet in the second chamber.

In a related embodiment, this invention provides for a process for oxidative coupling of methane to form ethylene, comprising:
(a) passing a flow of air through a first inlet into a first chamber defining a first flow passage;
(b) passing a flow of methane through a second inlet into a second chamber defining a second flow passage, wherein a porous medium having an oxidative coupling catalyst supported therein separates the first flow passage from the second flow passage;
(c) applying a pressure in the first flow passage sufficient to allow the air to flow via bulk flux through the porous medium into the second chamber;
(d) adjusting the flow of methane such that a ratio of diffusive flux of the methane into the porous medium to the bulk flux of the air through the porous medium is greater than 1:1;
(e) contacting the methane and the air at the oxidative coupling catalyst within the porous medium under reaction conditions sufficient to produce ethylene, which thereafter flows into the second flow passage and exits through an outlet in the second chamber.

In another embodiment, this invention provides for a process of oxidative dehydrogenation of a C2-10 alkane to form a corresponding C2-10 olefin having the same number of carbon atoms as the C2-10 alkane, comprising:
(a) passing a flow of an oxidant through a first inlet into a first chamber defining a first flow passage;
(b) passing a flow of the C2-10 alkane through a second inlet into a second chamber defining a second flow passage, wherein a porous medium having a dehydrogenation catalyst supported therein separates the first flow passage from the second flow passage;
(c) applying a pressure in the first flow passage sufficient to allow the oxidant to flow via bulk flux through the porous medium into the second chamber;
(d) adjusting the flow of the C2-10 alkane such that a ratio of diffusive flux of the C2-10 alkane into the porous medium to the bulk flux of the oxidant through the porous medium is greater than 1:1;
(e) contacting the C2-10 alkane and the oxidant at the oxidative coupling catalyst within the porous medium under reaction conditions sufficient to produce the corresponding C2-10 olefin having the same number of carbon atoms as the C2-10 alkane, which thereafter flows into the second flow passage and exits through an outlet in the second chamber.

As known in the art, the alkane is defined as an organic compound comprising carbon and hydrogen atoms wherein all of the carbon atoms are fully saturated, such that each carbon atom is involved in four single bonds, selected from carbon-hydrogen (C—H) and carbon-carbon (C—C) bonds. Alkanes do not comprise carbon-carbon double bonds (>C=C<) or carbon-carbon triple bonds (—C≡C—). In one embodiment relating to the oxidative coupling process of this invention, the alkane comprises a C1-4 alkane, exemplified by methane, ethane, propane, n-butane, isobutane, and mixtures thereof as illustrated by natural gas, shale gas, and refinery gas. In one exemplary embodiment, the alkane or mixture of alkanes further comprises a diluent comprising less than 50 volume percent of the non-alkane content, such diluents to include nitrogen ($N_2$), carbon dioxide ($CO_2$), hydrogen ($H_2$), carbon monoxide (CO), and mixtures thereof. In another exemplary embodiment, the alkane or mixture of alkanes does not comprise a diluent. In another embodiment relating to the oxidative dehydrogenation process of this invention, the alkane comprises a C2-10 alkane, exemplified by ethane, propane, butane, pentane, hexane, heptane, octane, nonane, decane, and mixtures thereof as illustrated by the aforementioned natural gas, shale gas, and refinery gas, including in any form of straight chain and branched chain structures.

For the purposes of this invention, the term "oxidant" is defined as a mixture comprising two components: an oxidizer and a diluent. Accordingly, for purposes of simplifying language used herein, the word "oxidant" refers inherently to the mixture of both the oxidizer and the diluent. The oxidizer generally comprises any oxidizing agent capable of removing hydrogen atoms from the alkane so as to produce an olefin (alkene). Oxygen ($O_2$) is a suitable oxidizer; less active but also suitable as oxidizers are sulfur compounds, for example, sulfur vapor, hydrogen sulfide, and methylsulfide. Suitable non-limiting examples of the oxidant's diluent include nitrogen, carbon dioxide and any inert gas including helium, neon, and argon, and mixtures thereof. In one exemplary embodiment, the oxidant comprises a mixture of oxygen and nitrogen, preferably air. In another exemplary embodiment, the oxidant comprises oxygen and carbon dioxide. Any operable dilution of oxidizer in the diluent is acceptable. In one illustrative embodiment, the oxidizer ranges from about 1 percent to 49 percent by volume relative to the volume of the diluent.

As known in the art, the product olefin or alkene is an organic compound comprising carbon and hydrogen atoms wherein at least one carbon-carbon bond is a double bond (C=C). The number of carbon atoms in the olefin product will depend upon whether the process conditions result in oxidative coupling products or dehydrogenation products. Oxidative coupling involves reactions wherein the reactant alkane and the oxidizer are contacted in the presence of an oxidative coupling catalyst to yield an olefin having double the number of carbon atoms as compared with the reactant alkane. Such as reaction is illustrated by Equation (1) hereinabove, wherein two methane molecules are coupled to form one ethylene molecule. Another illustration involves the oxidative coupling of two ethane molecules to form butene, as in Equation (5).

$$2C_2H_6 + O_2 \rightarrow C_4H_8 + 2H_2O \qquad \text{(Eqn. 5)}$$

More generically, the oxidative coupling process of this invention produces a C2-8 olefin; suitable examples of which include ethylene, propylene, butene, pentene, hexene, heptene, octene, and mixtures thereof, including in any of straight-chain, branched chain, cis- and trans-configurations.

In contrast, oxidative dehydrogenation involves processes wherein the reactant alkane and the oxidizer are contacted in the presence of an oxidative dehydrogenation catalyst to yield an olefin having the same number of carbon atoms as the reactant alkane. Such a reaction is illustrated by the oxidative dehydrogenation of propane to form propylene, as shown in Equation (6):

$$C_3H_8 + \tfrac{1}{2}O_2 \rightarrow C_3H_6 + H_2 \qquad \text{(Eqn. 6)}$$

Suitable examples of olefinic products produced via oxidative dehydrogenation include C2-10 olefins, namely, ethylene, propylene, butene, pentene, hexene, heptane, octene, nonene, decene, and mixtures thereof, including in any of straight-chain, branched chain, cis- and trans-configurations. Olefinic products comprising two or more carbon-carbon double bonds can also be formed, including for example, butadiene, pentadiene, hexadiene, heptadiene, and octadiene.

A molar ratio of alkane to oxidizer fed to the process is generally greater than about 1.9:1, preferably, greater than about 2:1, but also less than about 5:1. A preferred alkane/oxidizer mole ratio ranges from about 2.1:1 to about 2.5:1. The oxidant including the oxidizer and the diluent is fed into the reactor through a first inlet into a first flow chamber defining a first flow passage, which may be open-ended or close-ended at an end opposite the inlet end. Generally, the alkane is fed through a second inlet into a second chamber defining a second flow passage, which is open-ended and terminates at an exit of the second flow passage.

The porous medium separating the first and second chambers includes any solid framework or collection of solid struts that further comprises and defines a plurality of pores, channels, cavities, void spaces, or mixture thereof, which allows for a fluid flow path from a side adjacent the first chamber to an opposite side adjacent the second chamber. In one embodiment, the fluid flow path through the porous medium is regular or symmetrical as provided by a plurality of identical channels from first to second chambers. Thus, the medium provides a continuous porosity with essential uniformity (i.e., isotropic) in porosity and composition in all directions through the medium. In another embodiment, the fluid flow path through the medium from the first to second chambers is tortuous, winding in a serpentine manner from pore to channel to cavity, as the case may be. Accordingly, the medium can be constructed to be non-uniform normal or parallel to surfaces bounding the first and second chambers. One or more regions can have differing compositions or porosities; changes can be gradual or abrupt, or unevenly distributed, for the purposes of controlling pressure drop for control of bulk flow, for changing rates of diffusion for diffusive flow, or for changing reaction rates by controlling local availability of catalyst. In one exemplary embodiment, a first section of the porous medium closest the first flow passage consists of tight porosity, less than 2 microns average pore diameter, and consists of about 10 to 30 percent of the thickness of the porous medium. In this embodiment, the remaining section of the thickness of the porous medium is made with average pore diameter as noted hereinbelow. The first section can be made of a high-temperature metallic alloy or a ceramic and be free of catalyst; the second section can be constructed of ceramic or a high-temperature alloy, and contain catalyst. The transition between these two sections can be abrupt or gradual or irregular, as desired.

Additionally, the porous medium suitable for this invention is non-ion-conducting, which means that it essentially does not conduct or transport a flow of positive or negative ions, particularly, oxide ions, in response to an applied voltage or current. Rather, the porous medium suitable for this invention allows for bulk and diffusive flow of non-ionic organic compounds, particularly, alkanes and olefins in liquid or gaseous form, and oxidants and oxidizers in liquid or gaseous form.

Non-limiting examples of porous media suitable for this invention include porous ceramic materials, such as porous aluminas, silicas, aluminosilicates, titanium oxides, zirconium oxides, mullite, hexaluminates, and spinels, any of which can optionally include alkali and/or alkaline modifiers, such as lithium, sodium, potassium, barium, calcium, strontium, and mixtures thereof. Preferred porous media include aluminas and aluminosilicates, exemplified in one embodiment as 99 percent alumina and in another embodiment as 99.8 percent alumina, by weight. In another exemplary embodiment, the porous medium comprises a porous metal, illustrative species of which include stainless steel, iron-chromium-aluminum alloys and nickel-chromium-aluminum alloys. Typically, the pore, channel, cavity, or void space of the porous medium suitable for this invention has an average diameter or critical cross-sectional dimension ranging from about 2 microns (2 µm) to about 100 µm. Typically, the porous medium has a porosity of at least about 30 percent; in one embodiment, at least about 50 percent; in another embodiment, at least about 70 percent, defined as the percentage of void volume relative to total volume of the porous medium. Typically, the porous medium has a porosity less than about 90 percent.

The catalyst employed in this invention is chosen, as desired, for its activity and selectivity towards producing olefins through an oxidative coupling or oxidative dehydrogenation process, as exemplified in Equations 1, 5, and 6 hereinabove. Oxidative coupling catalysts suitable for this invention include any of those known in the art including compositions comprising magnesium, manganese, sodium tungstate, and silica ($Na/Mg/W/Mn/SiO_2$), in mixtures or various proportions with each metal (Na, Mg, W, Mn) present in amounts from 0-20 wt. % and in a metallic or oxide form; as well as compositions comprising lithium magnesium oxide (Li/MgO), or lanthanum oxide ($La_2O_3$), or strontium-magnesium-calcium-doped lanthanum oxide (Sr/Mg/Ca/$La_2O_3$), again in metallic or oxide form. Likewise, oxidative dehydrogenation catalysts useful for this invention include any known in the art, including any of the aforementioned oxidative coupling catalysts, as well as acid or sodium modified ZSM-5 (H/Na-ZSM-5), and rhenium, gallium, tungsten, and/or molybdenum modified ZSM-5 and MCM-22. Such catalysts are described by C. Karakaya and R. J. Kee, Progress in Energy and Combustion Science, Vol. 55 (2016), p. 60.

In this invention, the catalyst is disposed within the porous medium so as to infill a portion or essentially all of the porosity of the porous medium. Typically, the catalyst is sieved or ground into particles having a diameter smaller than the average pore size of the porous medium. The particles are then prepared into a slurry by suspension or dispersion in a suitable liquid, such as water, alcohol, or supercritical $CO_2$ or other liquids. The slurry is then dispersed into the void spaces of the porous medium after which the liquid is removed by appropriate heating or depressurization. Notably, the slurry is disposed into the porous medium by starting on the side of the medium adjacent the second flow passage (the side contacting the flow of alkane) and progressing through the thickness of the medium to its opposite side adjacent the first flow passage (the side contacting the flow of oxidant). In this manner, it was discovered that an optimum depth of catalyst provides for optimal selectivity and productivity for olefinic products without over-reaction to undesirable byproducts. Typically, the optimal depth of the catalyst slurry ranges from about 40 to about 60 percent of the thickness of the porous medium, measuring from the side adjacent the second flow passage to the side adjacent the first flow passage; although a depth to 100 percent of the thickness is operable if not entirely optimal.

Reference is now made to the attached Drawings where exemplary embodiments of the apparatus of this invention are depicted. FIG. 1 depicts in longitudinal cross-section one exemplary embodiment 100 of a single tubular apparatus and process of this invention. A porous medium is provided in the form of a porous ceramic tube 118 having a non-porous entry end 108 sealed and fitted with a ceramic plug 114 having a center hole. Within center hole of plug 114 is placed a ceramic or metallic tube 116 extending into an open interior, first chamber 124 of the porous tube 118. The opposite end 106 of porous tube 118 is sealed to prevent flow through the tube wall in non-porous region 106 and fitted with a solid ceramic plug 138 to prevent flow through its open end. The interior of porous tube 118 creates a first chamber 124 defining a first flow passage from an entrance at tube 116 to an exit through the porous tube 118. Within the unsealed portion of porous tube 118 is distributed a catalyst slurry so as to infill porous tube 118, fully or partially, creating catalyst containing region 110. In the embodiment illustrated in FIG. 1, region 102 of porous tube 118 is essentially free from catalyst and remains in its original porosity; although in another embodiment (not shown) the catalyst infills the entire porosity of tube 118. Surrounding the exterior of porous tube 118 is a solid non-porous tube 128 defining a second chamber 122 creating a second flow passage from an entrance at inlet 120 to an exit at outlet 126.

Further to FIG. 1, under operating conditions a flow of oxidant is fed through inlet tube 116 into the first chamber 124, where the oxidant is forced to pass under bulk flux through the porous tube 118 into the pathway of second chamber 122 and from thence to outlet 126. A flow of alkane is fed into the second chamber 122 through inlet 120, wherein the alkane diffuses into the porous tube 118. Upon contacting the alkane and the oxidizer in catalytic region 110 within porous tube 118, the alkane is converted into at least one olefin, which exits with the flow from the second chamber 122 via outlet 126. Note that in this embodiment, the diluent in the oxidant flows from the inner first chamber 124 through the porous tube 118 to the outer annular passage of second chamber 122. Under optimal reaction conditions, the oxidizer is essentially entirely consumed in catalyst area 110 and essentially does not enter the second chamber 122; while essentially no unreacted alkane enters the first chamber 124.

Figure 2:
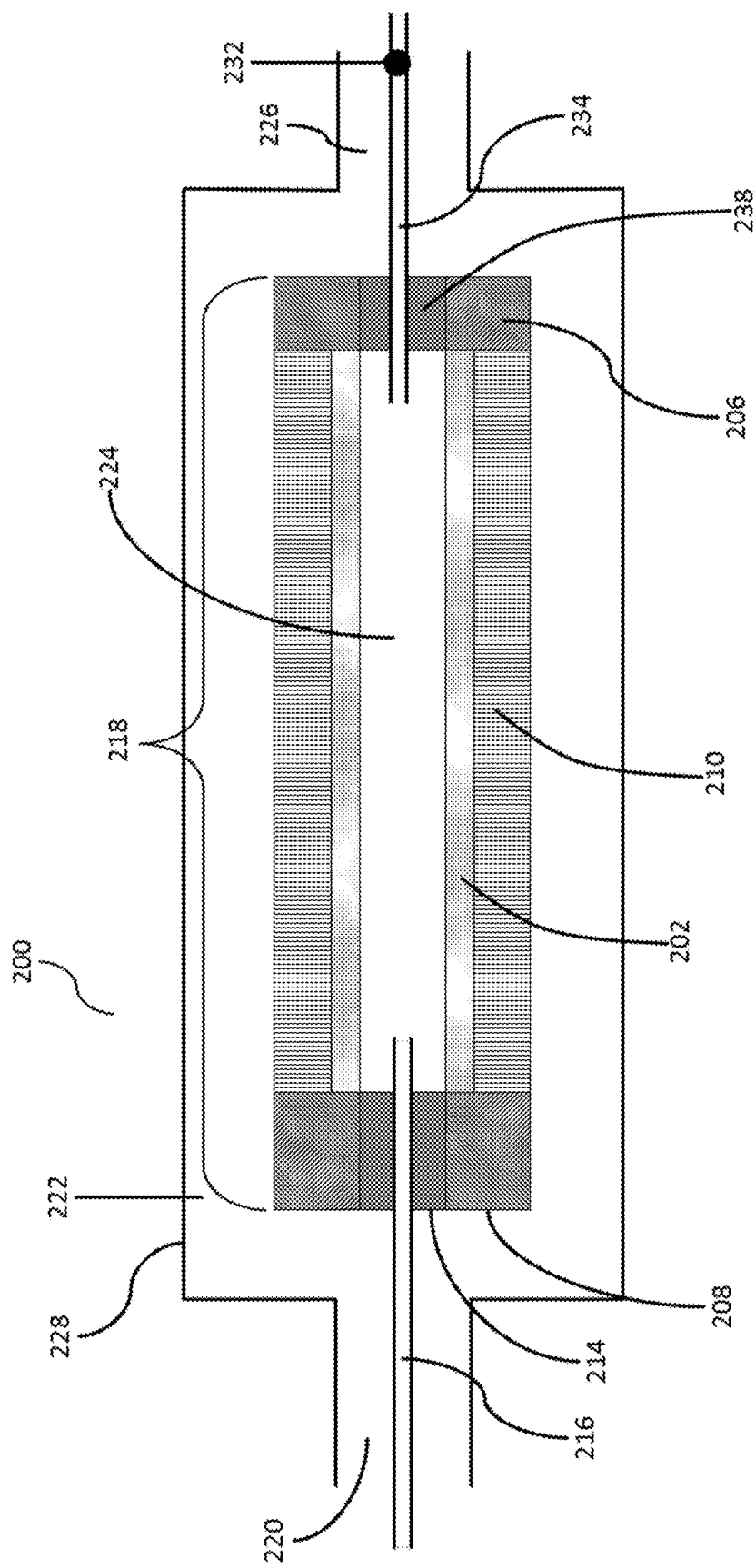
FIG. 2 depicts another exemplary embodiment of the process and a single tubular reactor apparatus of this invention.

FIG. 2 depicts in longitudinal cross-section another exemplary embodiment 200 of the reactor apparatus and process of this invention. A porous medium is provided in the form of a porous ceramic tube 218, having a non-porous entry end 208 sealed and fitted with a ceramic plug 214 having a center hole. Within center hole of plug 214 is placed a ceramic or metallic tube 216 extending into the open interior space 224 of the porous tube 218. The opposite end 206 of the porous tube 218 is sealed to prevent flow through the tube wall in region 206 and fitted with a solid ceramic plug 238 having a center hole. Through the center hole of plug 238 is placed another ceramic or metallic tube 234 having disposed therein a restriction or control valve 232. The interior of porous tube 218 creates a first chamber 224 defining a first flow passage for the oxidant from an entrance at tube 216 through porous tube 218. The oxidant flow may in part optionally exit through tube 234. Within the unsealed portion of porous tube 218 is distributed a catalyst slurry so as to infill porous tube 218, fully or partially, creating catalyst containing region 210. Region 202 of porous tube 218 is essentially free from catalyst and remains in its original porosity; although in another embodiment (not shown) the catalyst infills the entire porosity of tube 218. Surrounding the exterior of porous tube 218 is a solid non-porous tube 228 defining a second chamber 222 creating a second flow path from an entrance at inlet 220 to an exit at outlet 226. Under operating conditions, alkane and oxidant (oxidizer plus diluent) are fed in the manner described for FIG. 1. The bulk flux of oxidant is regulated by control valve 232. Products exit the reactor via outlet path 226. Optionally, unreacted oxidant exits via tube 234, not mixing with the flow passage 226.

With respect to FIGS. 1 and 2, it should be mentioned that in one exemplary embodiment, all components of the reactor are comprised of ceramic materials. In another exemplary embodiment, tubes 116, 216, and 234 are comprised of metallic materials, for example, stainless steel or any other alloy capable of withstanding the process temperature, illustrated for example by Inconel® and Hastalloy® brands of high temperature alloys. The non-porous housing 128 and 228 is in one embodiment ceramic, such as silica, or quartz for those portions adjacent to the tube 118 or 218, as the case may be; and the balance of the housing can be ceramic or metallic, as desired.

Figure 3:
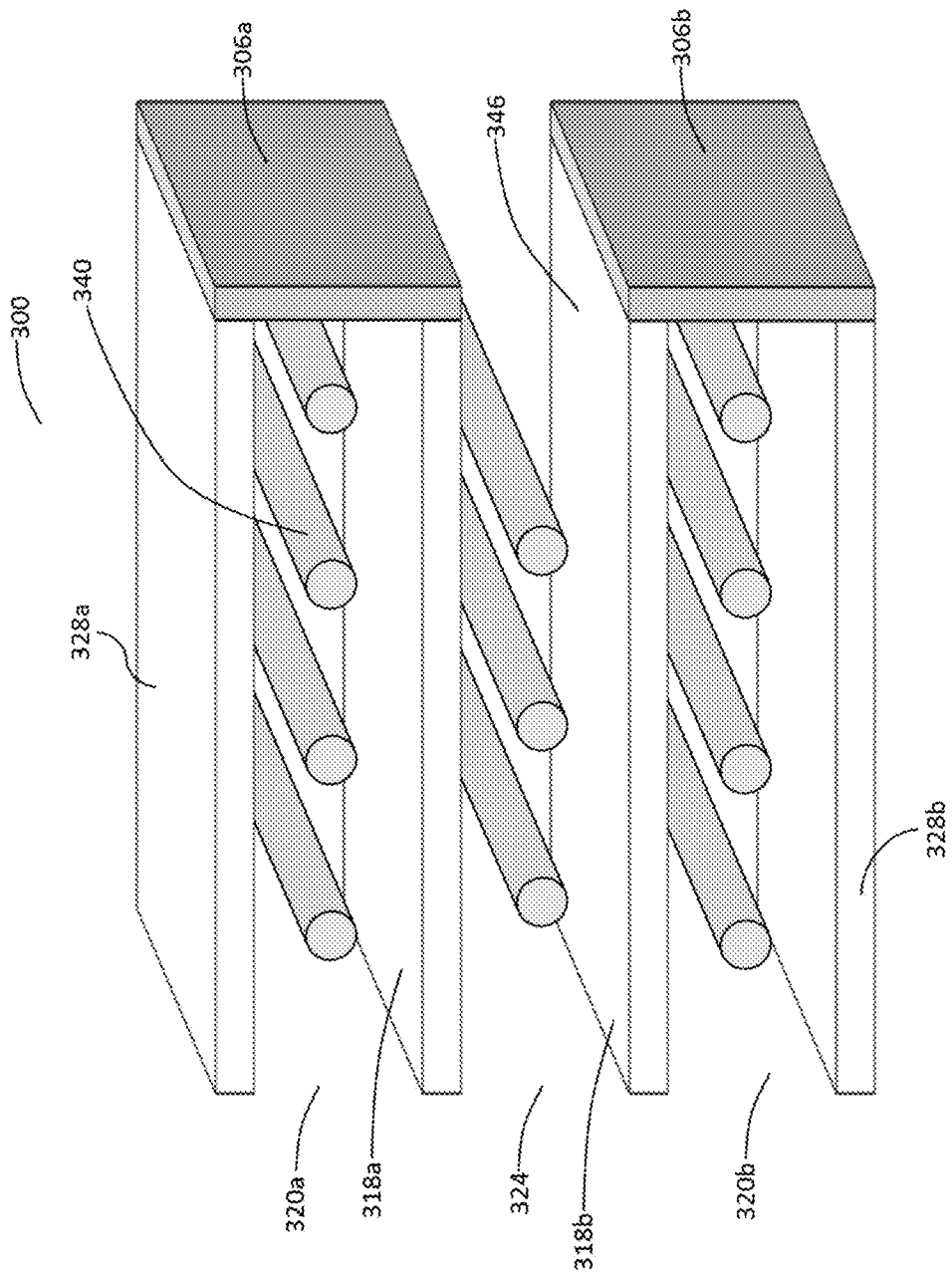
FIG. 3 depicts another exemplary embodiment of the process and a planar reactor apparatus of this invention further including heat exchangers.

FIG. 3 depicts in isometric view another exemplary embodiment 300 of the reactor and process of this invention, wherein the reactor is provided in a planar configuration. In FIG. 3, a plurality of layers, herein shown as four layers, are disposed in parallel alignment as follows: a first solid non-porous wall 328a, a first porous medium infilled with catalyst 318a, a second porous medium infilled with catalyst 318b, and a second solid non-porous wall 328b. Parallel layers 328a and 318a create a first flow passage from an inlet end 320a through the porous medium 318a inasmuch as the first flow passage outlet end 306a is sealed. Parallel layers 318a and 318b create a second flow passage from an inlet 324 to an outlet 346. Parallel layers 318b and 328b form another first flow passage from an inlet side 320b through porous wall 318b, inasmuch as outlet end 306b is also sealed. A plurality of heat exchange elements 340 are disposed in each of the flow passages 320a, 324, and 320b. Under operating conditions the oxidant is fed into flow passages 320a and 320b, passing under bulk flux through porous walls 318a and 318b, respectively, into second flow chamber 324. Alkane is fed into the second flow chamber 324 where it diffuses into porous media 318a and 318b contacting the oxidant and catalyst to produce olefinic products. Reaction products exit the second flow chamber through flow outlet 346.

Figure 4:
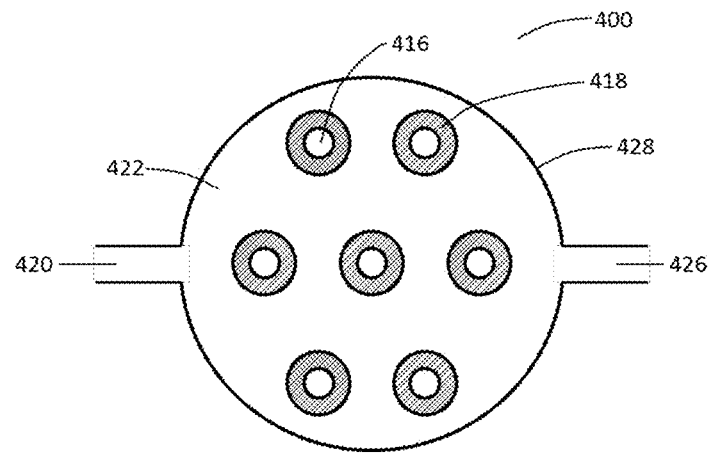
FIG. 4 depicts another exemplary embodiment of the process and apparatus of this invention comprising a plurality of tubular porous media disposed within a second flow path.

FIG. 4 depicts in transverse cross-section another exemplary embodiment 400 of the reactor apparatus and process of this invention, wherein a plurality of tubular porous media 418, defining a plurality of first flow paths 416, are disposed within a second flow path 422 bounded by a non-porous housing 428 having a flow inlet 420 and a flow outlet 426. Under reaction conditions the oxidant is fed into the plurality of flow inlets 416 passing via bulk flux through porous media 418 infilled with catalyst and from there into the second flow chamber 422. Alkane is fed through flow inlet 420, where it diffuses into the porous media 418 contacting the oxidizer and the catalyst. Chemical products exit via flow outlet 426.

Figure 5:
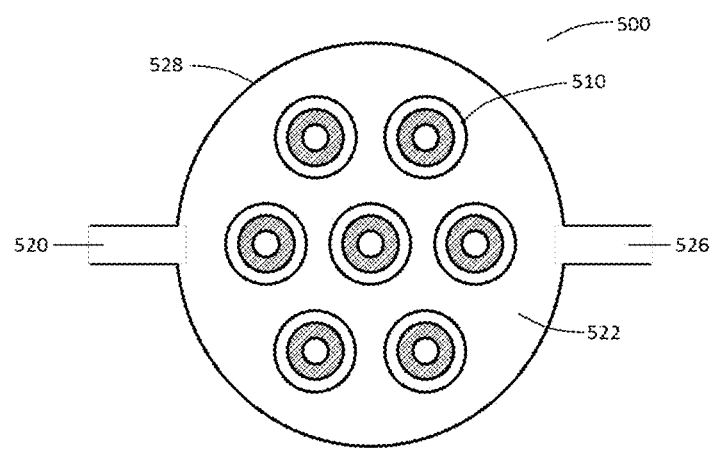
FIG. 5 depicts another exemplary embodiment of this invention comprising a plurality of reactors of this invention bundled into a heat exchange system.

FIG. 5 depicts in transverse cross-section another exemplary embodiment 500 of the process and apparatus of this invention wherein a plurality of single tubular reactors 510 of design similar to that shown in FIG. 1 or 2 are disposed within a large housing 528 having an inlet 520 and an outlet 526. Under operating conditions, a heat exchange fluid is passed through inlet 520 passing through plenum 522 and exiting through outlet 526. The heat exchange fluid is employed for purposes of controlling the temperature of the oxidative coupling or dehydrogenation process occurring within the tubular reactors 510.

Figure 6:
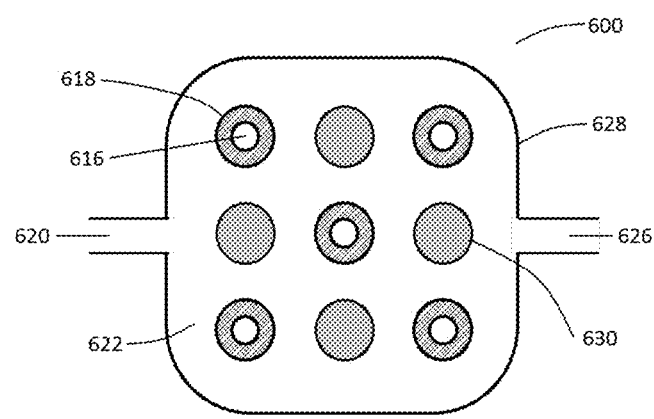
FIG. 6 depicts yet another exemplary embodiment of the process and apparatus of this invention comprising a plurality of tubular porous media and a plurality of heat exchangers disposed within a second flow path.

FIG. 6 illustrates in transverse cross-sectional view another embodiment 600 of the reactor and process of this invention, which is similar to the embodiment shown in FIG. 4, with the exception that a plurality of heat exchange tubes replace some of the air flow tubes. Thus, a plurality of tubular porous media 618 are disposed within a housing 628 having an inlet 620 and outlet 626. Under reaction conditions oxidant is fed into a plurality of flow inlets 616 passing via bulk flux through porous media 618 infilled with catalyst and from there into the second flow chamber 622. Alkane is fed through flow inlet 620, where it diffuses into the porous media 618 contacting the oxidizer and the catalyst. Chemical products exit via flow outlet 626. A plurality of heat exchange units 630 are disposed within the second flow path 622 for purposes of controlling the temperature of the oxidative coupling or dehydrogenation process occurring within reactor 600.

When the reactor of this invention is operated such that the diffusive flux of alkane into the porous medium is greater than the bulk flux of oxidant (i.e., mixture of oxidizer plus diluent) through the porous medium, then the advantages of the reactor are readily achieved. Using FIG. 1 as an example, the oxidant enters the reactor via inlet tube 116 passing into the first flow chamber defining the first flow passage 124, and thereafter is forced via bulk mass transport through the catalyzed porous tube 118. The alkane flows through inlet 120 and travels, via bulk mass transport or convective mass flow, through the second flow passage 122 to reactor outlet 126. The alkane, however, enters porous media 118 via diffusive flux from flow path 122. Heterogeneously catalyzed reactions of the alkane with the oxidizer take place over the catalyst within the porous medium 118. By maintaining the diffusive flux of alkane, expressed as moles alkane per square centimeter per second (mol/cm$^2$-sec), greater than the bulk flux of oxidant, also expressed in mol/cm$^2$-sec, then any tendency for overreaction of products and gas-phase reactions with the oxidizer, as illustrated by Equations 2-4, is minimized. Moreover, the selectivity to desired olefinic products, particularly two- and three-carbon containing olefins, more desirably ethylene, is maximized.

For purposes of this invention, bulk or convective flux is defined as a molar flow rate (mol/cm$^2$-sec) entering a catalyzed section in which area is defined as an inlet cross-sectional area of flow and is a result of forced or pressure-driven flow. For the tubular reactor embodiment of FIG. 1, the cross sectional area of flow is based on the inner circumference ("nD") of the porous medium 118 and the length of its porous section ("L") (that is, not counting non-porous sections 108, 114, 106, and 138). Sufficient pressure drop should be maintained such that flow channeling or flow bypassing is substantially avoided, while the flow is uniformly distributed through porous section of 118. The pressure drop between the first and second chambers is expressible as ΔP, which typically ranges from between about 0.1 psi (0.689 kPa) to 100 psi (689 kPa) with from about 1 psi (6.89 kPa) to 10 psi (68.9 kPa) more preferred.

For the purposes of this invention, diffusive flux is defined as the mass flow rate (mol/cm$^2$-sec) entering a catalyzed section in which a length is defined as the distance between the highest and lowest concentrations along a diffusion path; and therefore the mass flow rate is a result of a concentration gradient-driven flow. For the case of FIG. 1, the length ("Z") is the wall thickness of porous medium 118, with alkane being at its highest concentration in passageway 122 and at its lowest concentration in passageway 124. Passage 124 transporting the oxidant fed to the reactor has an alkane concentration of essentially zero; while passage 122, consisting of both alkane fed to the reactor and reaction products leaving the reactor, has an alkane concentration ranging from 100 percent at the end closest to the reactor inlet 120 to a lowest concentration occurring near the reactor outlet 126. An average alkane concentration can be used to estimate diffusive mass flux, which is given by Fick's law of diffusion (Equation 7, as referenced in "Transport Phenomena," R. Bird, W. Stewart and E. Lightfoot, J. Wiley & Sons, New York, 1960, p. 503):

$$J_A = -cD_{AB}dX_A/dz \qquad \text{(Eqn. 7)}$$

where "$J_A$" is the molar flux due to diffusion of species A, in this case alkane, given in units of mols alkane/cm$^2$-sec; "c" is the total concentration (mols/cm$^3$) of all chemical components in the diffusion volume. For example, when the alkane is methane and the oxidant is air, then "c" is the total concentration of methane, oxygen, nitrogen, and any reaction products including ethane, ethylene, higher alkanes and olefins, carbon monoxide, carbon dioxide, and water. "$D_{AB}$", given in units of cm$^2$/sec, is a binary diffusion coefficient (diffusivity) of species A (herein the alkane) in species B, herein approximated by the oxidant stream. If A is methane and the oxidant is air, then $D_{AB}$ is approximated as the diffusivity of methane in nitrogen; if the oxidant is oxygen, then $D_{AB}$ is approximated as the diffusivity of methane in oxygen. "$dX_A/dz$" is a differential concentration gradient, given in units of 1/cm, of species A along diffusion path having length "z". The differential $dX_A/dz$ can be linearized as $(X_{A,out}-X_{A,in})/z$, where "$X_{A,out}$" is the mole fraction of A (e.g., alkane) at the exit of the diffusion path z (measured in chamber 124), and is essentially zero; while "$X_{A,in}$" is the mole fraction of A (e.g., alkane) at the entrance to the diffusion path z (measured in chamber 122).

The binary diffusion coefficient, $D_{AB}$, can be obtained from tables available in the art, or alternatively, can be calculated according to equation 11-3.2 in "The Properties of Gases and Liquids," Fifth Ed., B. E. Poling, J. M. Prausnitz, J. P. O'Connell, McGraw-Hill, 2001, Ch. 11, using Leonard-Jones parameters tabulated in Lawrence Livermore National Laboratory publication UCRL-ID-139893, by L. D. Cloutman, Aug. 1, 2000. For a pressure of 1 atmosphere and 750° C., binary diffusion coefficients for methane in other components, as would be employed in one embodiment of the process of this invention where the alkane is methane and the oxidant is air, were calculated as set forth in Table 1. The most prevalent non-methane component in the gas mixture is nitrogen. Accordingly, methane diffusivity can be approximated by using the value of 1.83 cm$^2$/sec.

TABLE 1

Diffusivity of Methane in Component

| Component | cm$^2$/sec |
|---|---|
| $O_2$ | 1.86 |
| $N_2$ | 1.83 |
| $C_2H_4$ | 1.74 |
| $C_2H_6$ | 1.38 |
| $H_2$ | 5.78 |
| CO | 1.82 |
| $CO_2$ | 1.51 |
| $H_2O$ | 2.22 |

Based on the above calculation methods, a ratio of diffusive flux of the alkane into the porous medium to bulk flux of the oxidant through the porous medium ($DF_{ALK}:BF_{OX}$) is derived. In this invention, the ratio $DF_{ALK}:BF_{OX}$ is desirably greater than 1:1. In one embodiment, the ratio $DF_{ALK}:BF_{OX}$ is greater than about 10:1; in another embodiment, the ratio $DF_{ALK}:BF_{OX}$ is greater than about 20:1; in yet another embodiment, greater than about 40:1; and in yet another embodiment, greater than about 60:1. Typically, the ratio $DF_{ALK}:BF_{OX}$ is less than about 100:1. For a given alkane to oxidant feed ratio, the calculated ratio $DF_{ALK}:BF_{OX}$ varies with temperature; however, the variation is generally less than about 3 percent over a 150° C. range, and more typically, less than about 2 percent, as confirmed by examining Table 6 set forth in Example 4 hereinbelow.

In this invention any operable process temperature is employed provided that the alkane is converted to at least one olefin. A suitable process temperature is typically greater than about 500° C., preferably, greater than about 600° C., and more preferably greater than about 650° C. A suitable process temperature is typically less than about 900° C., preferably, less than about 850° C., and more preferably, less than about 800° C. For this invention, overall process pressure is defined as the pressure at the outlet of the second chamber, for example, outlet 126 (FIG. 1). In one embodiment, the overall pressure is greater than about 0.1 psi (0.69 kPa), in another embodiment, greater than about 0.5 psi (3.5 kPa), in yet another embodiment greater than about 10 psi (69 kPa). In one embodiment, the overall pressure is less than about 500 psi (3,450 kPa), in another embodiment, less than about 100 psi (690 kPa). The pressure at inlet 120 is somewhat higher (by about +1 psi to +5 psi) than the pressure at outlet 126. The pressure at inlet 116 is typically defined by a suitable ΔP over the pressure at outlet 126, the ΔP being sufficient to induce bulk flux of the oxidant through the porous medium, for example, at FIG. 1 (118). One suitable ΔP is about +2 psi (14 kPa) to +5 psi (35 kPa) greater than the pressure at the outlet of the second chamber, e.g., at outlet 126.

A flow rate of alkane and a flow rate of oxidant at the inlets to their respective flow paths are each independently described in terms of a weight hourly space velocity (g/g-cat/hr), calculated as grams alkane or oxidant per hour, as the case may be, divided by the gram-weight of the catalyst. In one embodiment a suitable flow rate for the alkane is greater than about 0.05 g/g-cat/hr, in another embodiment greater than about 0.1 g/g-cat/hr. In one embodiment a suitable flow rate for the alkane is less than about 240 g/g-cat/hr, in another embodiment less than about 40 g/g-cat/hr. In one embodiment a suitable flow rate for the oxidant (that is, the total flow of mixture of oxidizer and diluent) is greater than about 0.2 g/g-cat/hr, in another embodiment greater than about 1.2 g/g-cat/hr. In one embodiment a suitable flow rate for the oxidant is less than about 40 g/g-cat/hr, in another embodiment less than about 16 g/g cat/hr.

For the purpose of this invention, "Alkane conversion", calculated as a ratio based on molar flow rates, is defined as a difference between the flow rate of the alkane at the inlet to the reactor (second chamber) and flow rate of the alkane at the outlet of the reactor (second chamber) divided by the inlet alkane flow rate, as shown in Equation 8:

Conv ALK=(Alk IFR−Alk OFR)/(Alk IFR)     (Eqn. 8)

where "IFR" is the inlet flow rate, and "OFR" is the outlet flow rate.

For purposes of this invention, selectivity is provided as a ratio based on counting carbon atoms and is calculated as the outlet flow of carbon atoms contained in selected desired product(s) divided by a total outlet flow of non-feed carbon atoms. Using the oxidative coupling of methane to ethylene, ethane, and higher hydrocarbons as an example, the C2+ selectivity is calculated as the outlet flow rate of carbon atoms in hydrocarbon products containing two or more carbon atoms divided by the total outlet flow rate of carbon atoms excluding methane in the outlet flow, as shown in Equation 9.

Sel C2+=[2(ethylene OFR)+2(ethane OFR)+3(propylene OFR)+3(propane OFR)]/[(methane IFR)−(methane OFR)]     (Eqn. 9)

For this invention, the yield of any selected product(s) is defined as the multiplication product of the alkane conversion and the selectivity to desired product(s). Using the oxidative coupling of methane as an example, the yield of C2+ hydrocarbons is calculated as the multiplication product of the alkane conversion (Eqn. 8) and the selectivity to desired products (Eqn. 9), as illustrated below in Equation 10:

Yield C2+=(Conv. CH4)*(Sel. C2+)     (Eqn. 10)

For illustrative purposes the following exemplary embodiments are presented.

EMBODIMENTS

Example 1 (E-1)

Construction of a Reactor of the Invention: Aqueous manganese nitrate hydrate (Sigma-Aldrich) was mixed with silica (Davicat, $SiO_2$) followed by drying in air at 120° C. To the resulting powder was added an aqueous solution of sodium tungstate hydrate (Sigma-Aldrich) followed by drying in air at 120° C. To the resulting powder was added an aqueous solution of magnesium chloride hydrate (Sigma-Aldrich), followed by drying in air at 120° C. and then heat treating in air at 850° C. The final powder was crushed and sieved to particle sizes of less than 1 micron. The composition obtained, based on dry weights of starting materials, was 6% Mn, 20% $Na_2WO_4$, 3% Mg, and balance $SiO_2$, by weight.

The catalyst thusly prepared was combined with water to form a slurry containing in one embodiment (a) 15.2% by weight and in another embodiment (b) 7.6%, by weight, solids with the balance being water. Porous ceramic tubes composed of alumina (99 wt. percent) were obtained from Refractron, Inc., Newark, N.Y., with dimensions 400 mm length, 25 mm outer diameter (O.D.), and 15 mm inner diameter (I.D.). The tubes had an average pore diameter of 15 microns and a porosity of 54.6 percent, based on weight.

Starting at 25 mm from one end of the tube, each of two tubes was loaded along 203.2 mm of length with one sample of catalyst slurry, with the balance remaining uncatalyzed. (See Table 2.) After slurry addition, the tubes were dried in air at 95° C. and then heat treated in air at 300° C. Those portions of the tubes not containing catalyst were sealed by applying of Ceramabond™ brand 552-VFG paste (Aremco Products Inc., Valley Cottage, N.Y.). The open outlet end of the tube, 25 mm from the end of the catalyst section, was plugged with a solid alumina plug (McMaster-Carr), and then glued into place with the aforementioned paste. The inlet end of the tube was plugged with a solid alumina core leaving a 0.25" diameter hole into which was inserted a non-porous alumina tube (0.25" O.D. and 0.125" I.D., McMaster-Carr) and then sealed with the Ceramabond™ brand paste. The completed assembly was heat treated at 700° C.

FIG. 1 illustrates an embodiment of a single tubular reactor of this invention 100 constructed as described hereinabove, comprising a porous tube 118 having an entry end 108 sealed with paste and with a ceramic plug 114. Within a center hole of ceramic plug 114 was placed a ceramic tube 116 extending into a first flow chamber 124, namely, the interior of porous tube 118. The outlet end 106 of porous tube 118 was sealed to prevent flow through the tube wall in region 106, and the tube opening at end 106 was sealed with a solid ceramic plug 138. The catalyst slurry was loaded onto porous tube 118 so as to infill a portion 110 of tube 118 as measured from its outer surface. Remaining section 102 of porous tube 118 was free from catalyst and remained in its original porosity. Each tube, so constructed, was positioned, axially centered, inside a non-porous quartz tube 128 (3" dia.) having an inlet 120 at one end, an outlet 126 at the opposite end, creating a second chamber, an annular flow passage 122 from inlet 120 to outlet 126.

As shown in Table 2, reactor tubes B-E were prepared as described hereinabove. Table 2 lists the weight of catalyst solids loaded onto each tube and the depth of catalyst solids loaded, as measured from the outer surface (at outer diameter) to the inner surface (at inner diameter) of tube 118. Tubes B, C, and D represented intermediate depths of loading, while Tube E had catalyst solids fully loaded from outer to inner diameters of tube 118. For comparative purposes, Tube A was used as purchased with no heat treatments or catalyst materials added.

TABLE 2

| | Reactor Tubes | | |
|---|---|---|---|
| Tube | Wt. % catalyst solids in slurry deposited | Wt (g) catalyst solids loaded onto tube | Depth (mm) catalyst solids loaded |
| A (Comparative) | No Catalyst | 0 | 0 |
| B | 15.2 | 0.77 | 1.3 |
| C | 15.2 | 1.48 | 2.3 |
| D | 7.6 | 0.66 | 3.1 |
| E | 7.6 | 1.21 | 4.9 |

Example 2 (E-2)

Process According to This Invention: The reactor apparatuses prepared in Example 1 were each positioned inside a tube furnace (16") equipped with a temperature controller. Each reactor was tested individually according to the following procedure. The furnace was set to 700° C., 750° C., 800° C., or 850° C. With reference to FIG. 1, air was fed at a rate of 150 $cm^3$/min into the first chamber 124 via the first inlet 116. Methane was fed at a rate of 150 cm³/min (6.3 mmol/min) though the second chamber 122 defined as the annular space between the inner porous tube 118 and the outer non-porous tube 128. In both cases, the flow rates were referenced to 25° C. and 1 atm pressure standard conditions. Product analysis gas exiting outlet 126 was cooled and analyzed by gas chromatograph (Agilent Micro-GC) calibrated for analysis of oxygen, nitrogen, methane, hydrogen, carbon monoxide, carbon dioxide, ethylene, ethane, propylene, and propane. Water was removed from the product gas stream prior to analysis, and was determined by using a mass-balance relationship between the known inlet oxygen flow rate and measured outlet flow rates of oxygen, carbon dioxide and carbon monoxide. Table 3 tabulates reaction conditions, the calculated $DF_{CH4}:BF_{AIR}$ ratio at 750° C., and outcome including methane conversion (CH4 Conv), C2+ selectivity (C2+ Sel), and C2+ yield.

TABLE 3

| Reactor | $DF_{CH4}:BF_{AIR}$ | T (° C.) | CH4 Conv | C2+ Sel | C2+ Yield |
|---|---|---|---|---|---|
| 2-A | x | 700 | 0.066 | 0.075 | 0.005 |
| 2-A | x | 750 | 0.104 | 0.098 | 0.010 |
| 2-A | x | 800 | 0.134 | 0.172 | 0.023 |
| 2-B | | 700 | 0.115 | 0.486 | 0.056 |
| 2-B | 66.5 | 750 | 0.148 | 0.426 | 0.063 |
| 2-B | | 800 | 0.165 | 0.455 | 0.075 |
| 2-C | | 700 | 0.114 | 0.430 | 0.049 |
| 2-C | 36.5 | 750 | 0.142 | 0.450 | 0.064 |
| 2-C | | 800 | 0.169 | 0.436 | 0.074 |
| 2-C | | 850 | 0.177 | 0.398 | 0.071 |
| 2-D | | 700 | 0.153 | 0.555 | 0.085 |
| 2-D | 27.6 | 750 | 0.157 | 0.501 | 0.079 |
| 2-D | | 800 | 0.168 | 0.455 | 0.077 |
| 2-E | | 700 | 0.087 | 0.399 | 0.035 |
| 2-E | 17.2 | 750 | 0.143 | 0.372 | 0.053 |
| 2-E | | 800 | 0.167 | 0.411 | 0.069 |

(a) Methane Flow Rate, 150 cm³/min; air flow rate 150 cm³/min, at standard conditions.
(b) Comparative: 2-A, no catalyst; Examples with catalyst: 2-B, C, D, and E.

Figure 7:
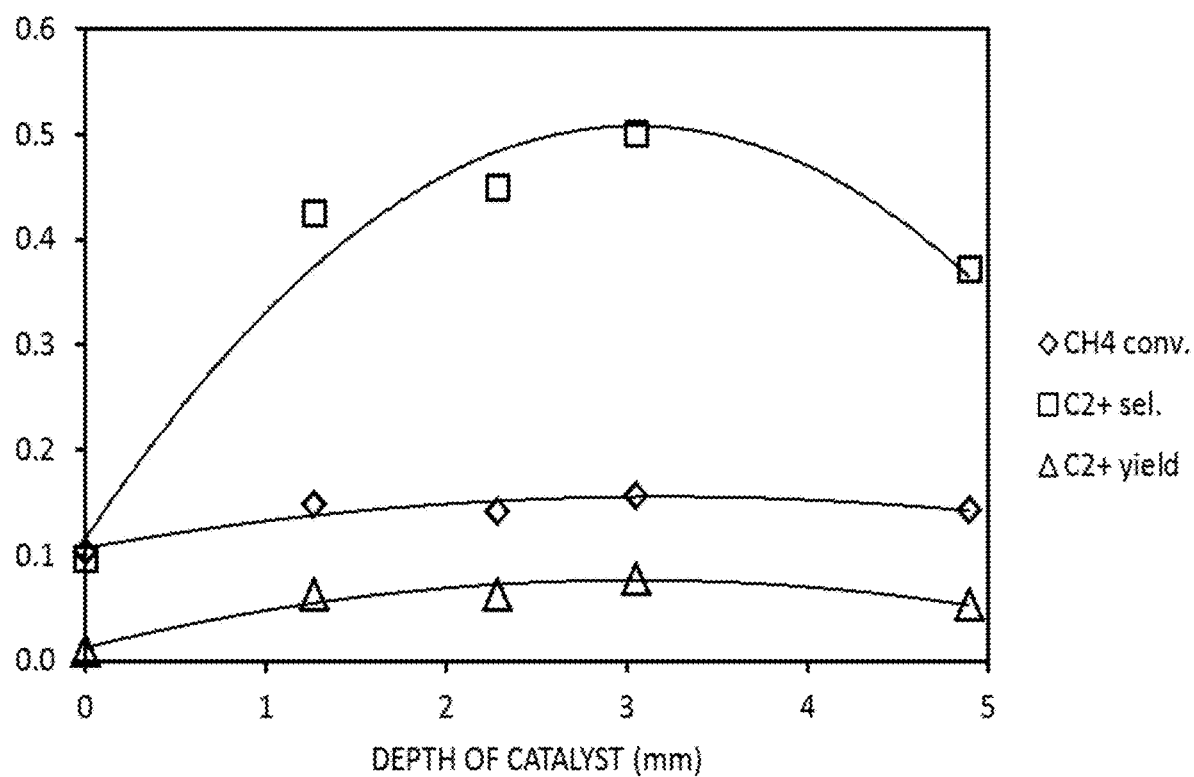
FIG. 7 depicts a graph plotting methane conversion, C2+ selectivity, and C2+ yield as a function of depth of catalyst for an embodiment of the process of this invention operating at 750° C.

FIG. 7 presents a plot of CH4 Conv C2+ Sel and C2+ Yield versus depth of catalyst at 750° C. From FIG. 7, it is seen that alkane conversion, C2+ selectivity, and C2+ yield are maximized at an optimum depth (3 mm) of catalyst in the porous medium. Similar results were obtained when the data were collected at 700° C. and 800° C. and plotted.

Figure 9:
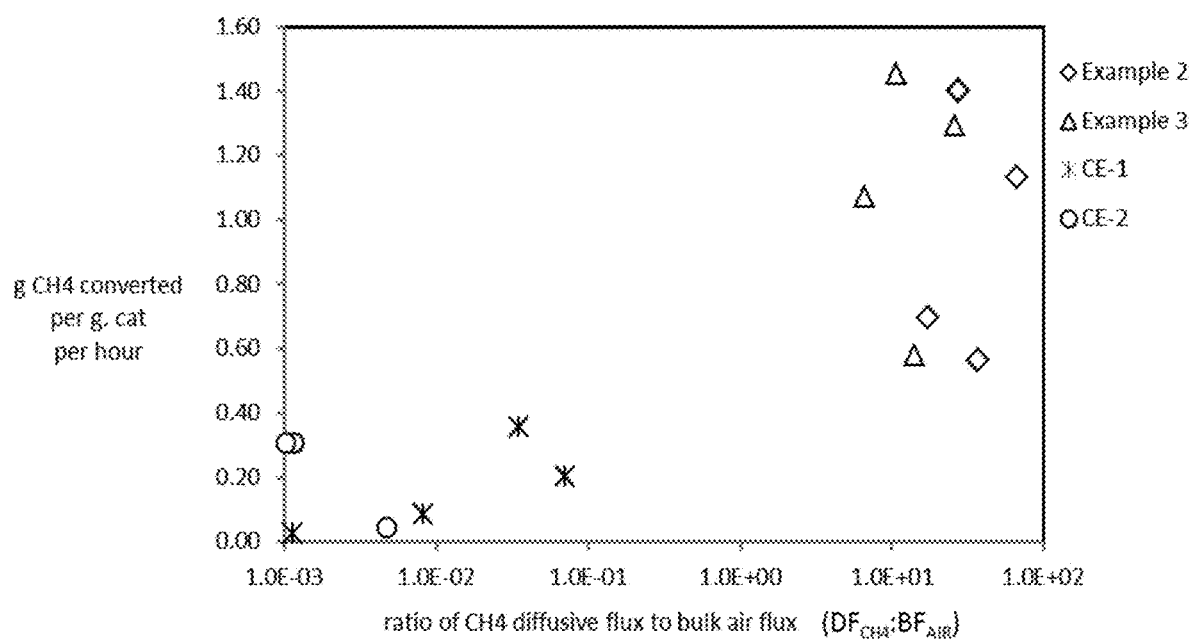
FIG. 9 depicts a graph plotting grams methane converted per gram catalyst per hour as a function of a ratio of methane diffusive flux to air bulk flux ($DF_{CH4}:BF_{AIR}$).
Figure 10:
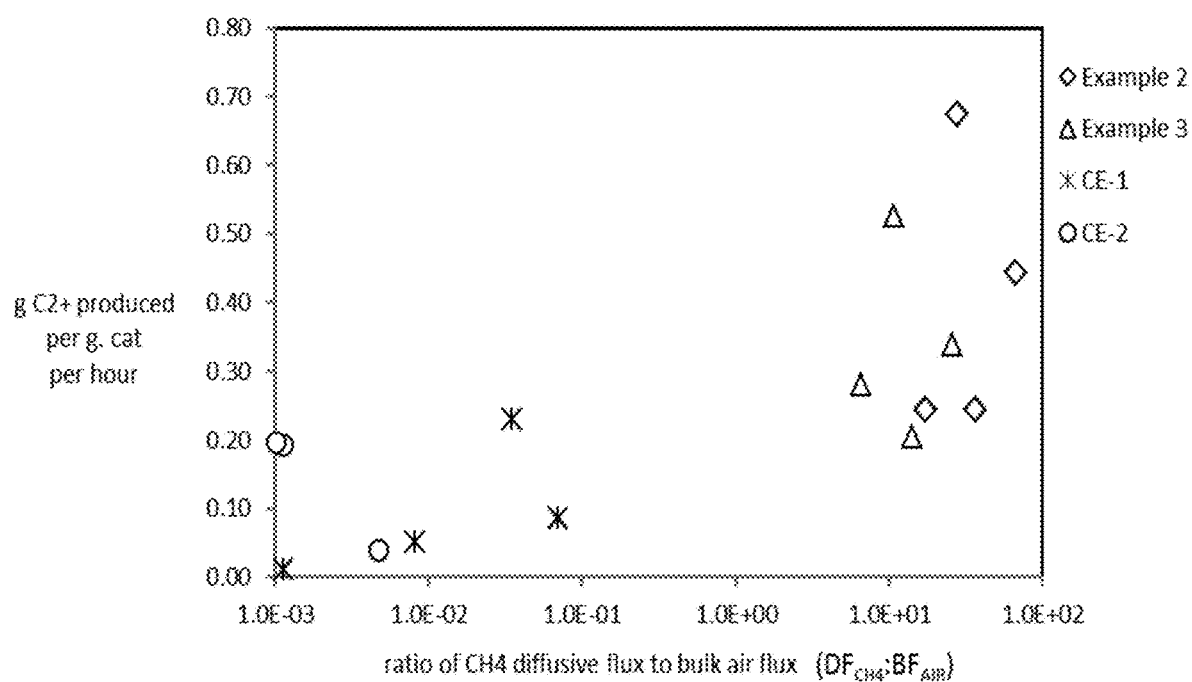
FIG. 10 depicts a graph plotting productivity, in units of grams C2+ products produced per gram catalyst per hour, as a function of the ratio $DF_{CH4}:BF_{AIR}$.

FIG. 9 (E-2) depicts a plot of weight CH4 converted as a function of the ratio $DF_{CH4}:BF_{AIR}$. FIG. 10 (E-2) depicts a plot of C2+ productivity as a function of the ratio $DF_{CH4}:BF_{AIR}$. These figures further illustrate the effectiveness of the process and reactor operated according to this invention, in terms of effective utilization of the catalyst and productivity for desired product.

Example 3 (E-3)

Figure 8:
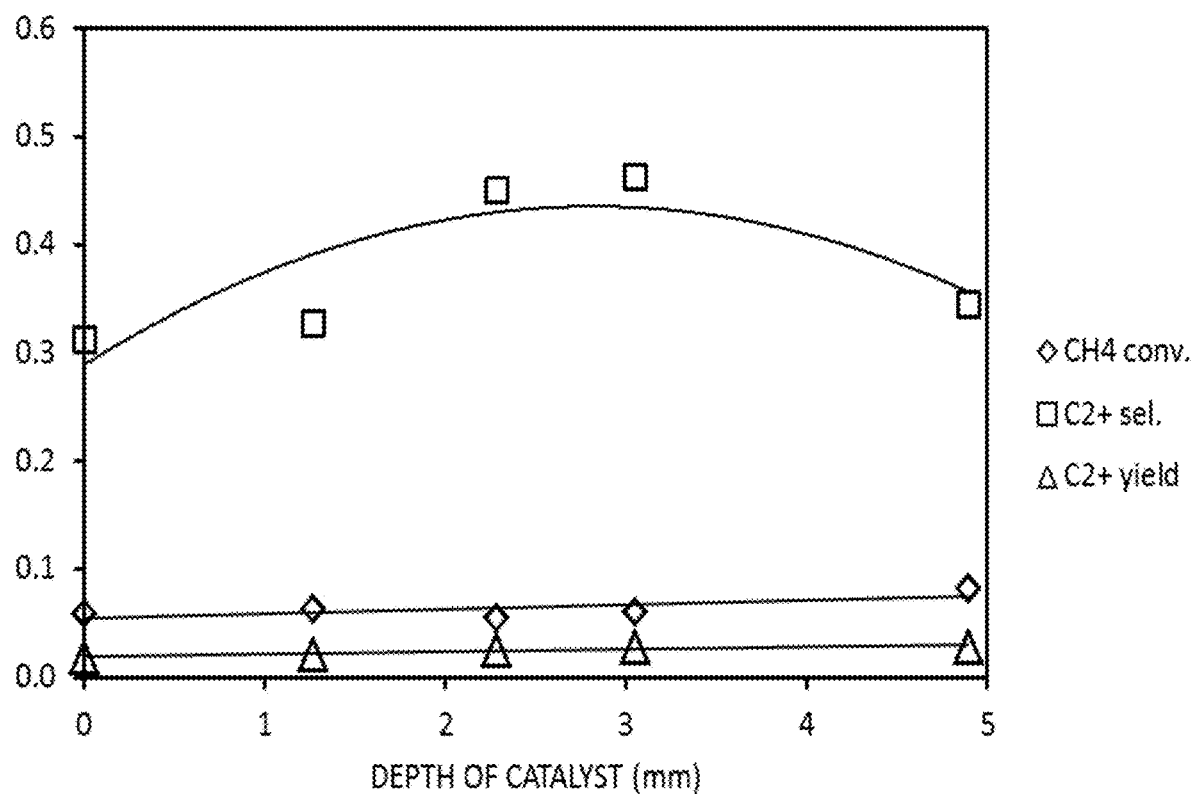
FIG. 8 depicts a graph plotting methane conversion, C2+ selectivity, and C2+ yield as a function of depth of catalyst for another embodiment of the process of this invention operating at 750° C.

Example 2 was repeated, except that the flow rates of methane and air were each set at 400 cm³/min (16.35 mmol/min inlet methane flow rate). Table 4 tabulates process conditions, the calculated ratio $DF_{CH4}:BF_{AIR}$ at 750° C., and process output results. FIG. 8 presents plots of CH4 Conv, C2+ Sel, and C2+ Yield versus depth of catalyst at 750° C.

TABLE 4

| Reactor | $DF_{CH4}:BF_{AIR}$ | T (° C.) | CH4 conv. | C2+ sel. | C2+ yield |
|---|---|---|---|---|---|
| 3-A | x | 700 | 0.034 | 0.250 | 0.009 |
| 3-A | x | 750 | 0.059 | 0.313 | 0.019 |
| 3-A | x | 800 | 0.104 | 0.389 | 0.040 |
| 3-A | x | 850 | 0.162 | 0.353 | 0.057 |
| 3-B | | 700 | 0.030 | 0.250 | 0.007 |
| 3-B | 25.8 | 750 | 0.064 | 0.328 | 0.021 |
| 3-B | | 800 | 0.143 | 0.363 | 0.052 |
| 3-B | | 850 | 0.190 | 0.404 | 0.077 |
| 3-C | | 700 | 0.025 | 0.316 | 0.008 |
| 3-C | 14.2 | 750 | 0.055 | 0.452 | 0.025 |
| 3-C | | 800 | 0.120 | 0.486 | 0.058 |
| 3-C | | 850 | 0.185 | 0.422 | 0.078 |
| 3-D | | 700 | 0.027 | 0.320 | 0.009 |
| 3-D | 10.8 | 750 | 0.061 | 0.463 | 0.028 |
| 3-D | | 800 | 0.134 | 0.489 | 0.066 |
| 3-D | | 850 | 0.193 | 0.420 | 0.081 |
| 3-E | | 700 | 0.044 | 0.224 | 0.010 |
| 3-E | 6.62 | 750 | 0.082 | 0.345 | 0.028 |
| 3-E | | 800 | 0.142 | 0.406 | 0.058 |
| 3-E | | 850 | 0.191 | 0.405 | 0.077 |

(a) Methane Flow Rate, 400 cm³/min; air flow rate 400 cm³/min, at standard conditions.
(b) Comparative: 3-A, no catalyst; Examples with catalyst: 3-B, C, D, and E.

From FIG. 8, it is seen that CH4 conversion, C2+ selectivity, C2+ yield are all maximized at an optimum depth of catalyst in the porous tube (between 3 mm and 5 mm). Similar results were obtained when the data were collected at 700° C., 800° C., and 850° C. and plotted.

FIG. 9 (E-3) depicts a plot of weight CH4 converted as a function of the ratio $DF_{CH4}:BF_{AIR}$. FIG. 10 (E-3) depicts a plot of C2+ productivity as a function of the ratio $DF_{CH4}:BF_{AIR}$. These figures further illustrate the effectiveness of the process and reactor operated according to this invention, in terms of effective utilization of the catalyst and productivity for desired product.

Example 4 (E-4)

Several reactor apparatuses were prepared and tested in accordance with the invention in a manner similar to Examples 1 and 2 and FIG. 1. Each reactor was prepared using a porous tube (400 mm length, 25 mm O.D., 16 mm I.D., 0.546 porosity) with a catalyzed length of 203.2 mm, and a ceramic oxidant inlet tube (0.25 inch O.D.). Properties of prepared tubes 4A-C are listed in Table 5. Additionally, Reactor 2-D was subjected with this group to further testing.

TABLE 5

| Reactor | Wt. of catalyst loaded into porous tube (g) | Depth of catalyst (mm) | Porosity in portion containing catalyst | bulk flow area (cm²) |
|---|---|---|---|---|
| 4-A | 3.02 | 3.1 | 0.528 | 102.1 |
| 4-B | 1.24 | 3.6 | 0.536 | 102.1 |
| 4-C | 5.89 | 3.6 | 0.501 | 102.1 |
| 2-D | 0.66 | 3.0 | 0.541 | 102.1 |

The process was run in Reactors 4A-C and 2-D at temperatures of 700° C. to 850° C., at a $CH_4:O_2$ mole ratio ranging from 2:1 to 10:1 and at different methane inlet flow rates. In all cases air was introduced through the porous inner tube, and methane was introduced into the annular space between the porous inner tube and the non-porous outer tube. Using methods described in the art as noted hereinabove, the values of the $CH_4$—$N_2$ binary diffusion coefficient were calculated to be 1.684 cm²/sec, 1.832 cm²/sec, 1.984 cm²/sec, and 2.141 cm²/sec at 700° C., 750° C., 800° C., and 850° C., respectively. Using these numbers, the ratio $DF_{CH4}:BF_{AIR}$ was calculated using the methods described hereinabove. Table 6 lists test conditions and process results.

TABLE 6

| Rx 4 | T °C. | g CH$_4$ feed per g cat-hr | Feed CH$_4$/O$_2$ mole ratio | CH4 conv. | C2+ sel. | C2+ yield | gC2+ per g cat-hr | gCH$_4$ conv per g cat-hr | Ratio DF$_{CH4}$:BF$_{AIR}$ |
|---|---|---|---|---|---|---|---|---|---|
| A | 700 | 1.12 | 1.92 | 0.172 | 0.151 | 0.026 | 0.193 | 0.026 | 15.7 |
| A | 750 | 1.12 | 1.92 | 0.319 | 0.247 | 0.079 | 0.357 | 0.075 | 15.7 |
| A | 800 | 1.12 | 1.92 | 0.395 | 0.232 | 0.091 | 0.443 | 0.085 | 15.9 |
| A | 700 | 1.96 | 4.77 | 0.092 | 0.299 | 0.027 | 0.180 | 0.048 | 26.4 |
| A | 750 | 1.96 | 4.77 | 0.169 | 0.384 | 0.065 | 0.331 | 0.106 | 26.5 |
| A | 800 | 1.96 | 4.77 | 0.204 | 0.381 | 0.078 | 0.398 | 0.123 | 26.9 |
| A | 700 | 2.61 | 9.55 | 0.054 | 0.277 | 0.015 | 0.141 | 0.036 | 44.5 |
| A | 750 | 2.61 | 9.55 | 0.059 | 0.637 | 0.037 | 0.153 | 0.084 | 45.4 |
| A | 800 | 2.61 | 9.55 | 0.083 | 0.639 | 0.053 | 0.216 | 0.110 | 46.2 |
| B | 700 | 2.74 | 1.92 | 0.178 | 0.163 | 0.029 | 0.487 | 0.072 | 13.7 |
| B | 750 | 2.74 | 1.92 | 0.303 | 0.220 | 0.067 | 0.829 | 0.156 | 13.8 |
| B | 800 | 2.74 | 1.92 | 0.391 | 0.228 | 0.089 | 1.069 | 0.202 | 13.9 |
| B | 700 | 4.77 | 4.77 | 0.068 | 0.240 | 0.016 | 0.324 | 0.071 | 23.3 |
| B | 750 | 4.77 | 4.77 | 0.137 | 0.351 | 0.048 | 0.654 | 0.196 | 23.4 |
| B | 800 | 4.77 | 4.77 | 0.197 | 0.348 | 0.069 | 0.939 | 0.267 | 23.6 |
| B | 700 | 6.36 | 9.55 | 0.013 | 0.788 | 0.010 | 0.085 | 0.062 | 39.2 |
| B | 750 | 6.36 | 9.55 | 0.047 | 0.695 | 0.033 | 0.300 | 0.180 | 39.9 |
| B | 800 | 6.36 | 9.55 | 0.083 | 0.627 | 0.052 | 0.526 | 0.266 | 40.4 |
| C | 700 | 0.57 | 1.92 | 0.414 | 0.353 | 0.146 | 0.237 | 0.070 | 12.1 |
| C | 750 | 0.57 | 1.92 | 0.423 | 0.362 | 0.153 | 0.243 | 0.073 | 12.5 |
| C | 800 | 0.57 | 1.92 | 0.418 | 0.314 | 0.131 | 0.240 | 0.062 | 12.9 |
| C | 700 | 1.00 | 4.77 | 0.185 | 0.369 | 0.068 | 0.185 | 0.058 | 20.9 |
| C | 750 | 1.00 | 4.77 | 0.212 | 0.453 | 0.096 | 0.212 | 0.079 | 21.4 |
| C | 800 | 1.00 | 4.77 | 0.218 | 0.464 | 0.101 | 0.219 | 0.081 | 22.0 |
| C | 700 | 1.34 | 9.55 | 0.070 | 0.569 | 0.040 | 0.093 | 0.047 | 35.8 |
| C | 750 | 1.34 | 9.55 | 0.088 | 0.714 | 0.063 | 0.117 | 0.070 | 36.7 |
| C | 800 | 1.34 | 9.55 | 0.096 | 0.719 | 0.069 | 0.129 | 0.073 | 37.7 |
| C | 700 | 2.67 | 2.01 | 0.098 | 0.075 | 0.007 | 0.261 | 0.018 | 3.0 |
| C | 750 | 2.67 | 2.01 | 0.194 | 0.294 | 0.057 | 0.517 | 0.135 | 3.0 |
| C | 800 | 2.67 | 2.01 | 0.376 | 0.360 | 0.135 | 1.004 | 0.306 | 2.9 |
| C | 850 | 2.67 | 2.01 | 0.392 | 0.298 | 0.117 | 1.048 | 0.258 | 3.0 |
| C | 700 | 2.67 | 4.77 | 0.091 | 0.183 | 0.017 | 0.243 | 0.041 | 8.1 |
| C | 750 | 2.67 | 4.77 | 0.178 | 0.393 | 0.070 | 0.476 | 0.161 | 8.1 |
| C | 800 | 2.67 | 4.77 | 0.222 | 0.445 | 0.099 | 0.592 | 0.217 | 8.2 |
| 2D | 700 | 5.11 | 1.92 | 0.173 | 0.143 | 0.025 | 0.885 | 0.114 | 16.4 |
| 2D | 750 | 5.11 | 1.92 | 0.318 | 0.219 | 0.070 | 1.625 | 0.303 | 16.3 |
| 2D | 800 | 5.11 | 1.92 | 0.397 | 0.232 | 0.092 | 2.030 | 0.392 | 16.5 |
| 2D | 700 | 8.92 | 4.77 | 0.076 | 0.196 | 0.015 | 0.680 | 0.123 | 27.7 |
| 2D | 750 | 8.92 | 4.77 | 0.146 | 0.329 | 0.048 | 1.305 | 0.366 | 27.9 |
| 2D | 800 | 8.92 | 4.77 | 0.204 | 0.371 | 0.076 | 1.815 | 0.546 | 28.1 |
| 2D | 700 | 11.89 | 9.55 | 0.018 | 0.627 | 0.011 | 0.218 | 0.126 | 46.7 |
| 2D | 750 | 11.89 | 9.55 | 0.050 | 0.697 | 0.035 | 0.596 | 0.356 | 47.4 |
| 2D | 800 | 11.89 | 9.55 | 0.087 | 0.685 | 0.060 | 1.033 | 0.565 | 48.1 |

Comparative Experiment 1 (CE-1)

For comparative purposes, a portion of the catalyst prepared in Example 1 was loaded into a packed bed reactor (tubular quartz tube, 3.2 cm I.D.) held in place with quartz wool and tested in the oxidative coupling of methane with air. Catalyst particles were screened to particle diameters no larger than 120 microns. Weights of catalyst tested were 30, 2, and 10 grams, with the 30 gram catalyst bed further diluted with 30 grams of equivalently sized quartz particles, yielding bed heights of 45 cm, 1.5 cm, and 7.5 cm, respectively. Each reactor assembly was placed into a tube furnace equipped with temperature control, and held at 750° C. The CH4:O2 mole ratio was held at 4.77:1; methane flow rates are specified in Table 7. To avoid excess heat generation and maintain catalyst temperatures, the air and methane flows were diluted with nitrogen gas at a flow rate equivalent to the inlet methane flow rate. Process conditions and results are presented in Table 7. FIG. 9 (CE-1) plots the g CH4 converted per gram catalyst per hour as a function of the ratio DF$_{CH4}$:BF$_{AIR}$. FIG. 10 (CE-1) plots the g C2+ produced as a function of the ratio DF$_{CH4}$:BF$_{AIR}$.

TABLE 7

| CE-1 | catalyst wt. (g) | CH4 inlet flow rate (mmols/min) | DF$_{CH4}$: DB$_{AIR}$ | CH4 conv. | C2+ sel. | C2+ yield | gCH4 Conv per g cat-hr | gC2+ yield per g cat-hr |
|---|---|---|---|---|---|---|---|---|
| A | 30.0 | 4.09 | 0.0011 | 0.20 | 0.59 | 0.12 | 0.027 | 0.012 |
| B | 2.0 | 2.04 | 0.0704 | 0.21 | 0.58 | 0.12 | 0.200 | 0.086 |
| C | 2.0 | 4.09 | 0.0353 | 0.18 | 0.62 | 0.11 | 0.360 | 0.230 |
| D | 10.0 | 4.09 | 0.0082 | 0.22 | 0.63 | 0.14 | 0.087 | 0.051 |

By comparing Examples 2 and 3 with CE-1, it is seen that the conversion of methane and productivity to C2+ products were greatly enhanced on a per catalyst weight basis by employing the apparatus and process of this invention as compared with using a packed bed reactor.

Comparative Experiment 2 (CE-2)

For comparative purposes, the oxidative coupling of methane with air was conducted in an annular packed bed reactor constructed as follows: Along an axial length of an interior space of a quartz tube (3.2 cm I.D.) was placed a solid quartz rod (2.5 cm dia.), providing for an annular gap (0.35 cm length) around the circumference of the quartz rod, between the rod and tube. Catalyst (5 g) prepared as in Example 1 was filled into the gap, producing a catalyst bed of height 6 cm. Three tests at the methane flow rates indicated in Table 8 were conducted, tested at 750° C. and a $CH_4:O_2$ mole ratio of 4.77:1, with experiments CE-2A and CE-2B employing additional flows of nitrogen gas at flow rates equivalent to the inlet methane flow rates. Process conditions and results are presented in Table 8. For these results, FIG. 9 (CE-2) plots the g CH4 converted per gram catalyst per hour as a function of the ratio $DF_{CH4}:BF_{AIR}$. FIG. 10 (CE-2) plots the g C2+ produced as a function of the ratio $DF_{CH4}:BF_{AIR}$.

TABLE 8

| CE-2 | CH4 inlet flow rate (mmols/min) | $DF_{CH4}:DB_{AIR}$ | CH4 conv. | C2+ sel. | C2+ yield | gCH4 Conv per g cat-hr | gC2+ yield per g cat-hr |
|---|---|---|---|---|---|---|---|
| A | 10.2 | 0.0011 | 0.16 | 0.54 | 0.09 | 0.310 | 0.190 |
| B | 2.04 | 0.0047 | 0.12 | 0.57 | 0.07 | 0.046 | 0.039 |
| C | 16.3 | 0.0010 | 0.10 | 0.47 | 0.05 | 0.310 | 0.200 |

By comparing Examples 2 and 3 hereinabove with CE-2, it was seen that the conversion of methane and productivity to C2+ products were greatly enhanced on a per catalyst weight basis by employing the apparatus and process of this invention, as compared with using the annular packed bed reactor.

Example 5 (E-5)

An additional tube was prepared and tested for conversion of ethane ($C_2H_6$) to ethylene ($C_2H_4$) via oxidative dehydrogenation with oxygen contained in air. Catalyst loading and testing procedures were similar to those used in catalyzed tubes prepared in Example 2 and tested in Examples 3 or 4. Specifically in this example, a 400 mm long porous tube (0.51 porosity, 25 mm outer diameter and 16 mm inner diameter) was used with sealing and 0.25" ceramic tube insert as described in Example 2; with a catalyzed length of 203.2 mm, 2.49 grams of catalyst, and with a 3.0 mm depth, as measured from the outer surface of the tube. The porous tube so prepared was installed into a non-porous tube in the manner illustrated in FIG. 1 and was tested from temperatures of 600° C. to 800° C. at a $C_2H_6/O_2$ mole ratio of 2.0:1 and at an $C_2H_6$ flow rate of 6.69 mmol/min. Air was introduced through the porous inner tube and ethane introduced into the annular space between the porous inner tube and the non-porous outer tube. Results are summarized in Table 9, expressed as fractional values between 0 and 1.

TABLE 9

| (° C.) | C2H6 conv. | C2H4 sel. | C2H4 yield | gC2H4/g cat/hr |
|---|---|---|---|---|
| 600 | 0.243 | 0.203 | 0.049 | 0.39 |
| 650 | 0.281 | 0.307 | 0.086 | 0.68 |
| 700 | 0.398 | 0.543 | 0.216 | 2.13 |
| 750 | 0.641 | 0.708 | 0.454 | 4.65 |
| 800 | 0.877 | 0.697 | 0.612 | 5.71 |

While the invention has been described in detail in connection with only a limited number of embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A process of oxidative coupling for converting an alkane to an olefin having twice the number of carbon atoms as the alkane, comprising:
    (a) passing a flow of an oxidant through a first inlet into a first chamber defining a first flow passage;
    (b) passing a flow of an alkane through a second inlet into a second chamber defining a second flow passage, wherein a porous medium having an oxidative coupling catalyst supported therein separates the first flow passage from the second flow passage, wherein the oxidative coupling catalyst infills the porous medium at a depth from 40 to 60 percent of the thickness of the porous medium measuring from a side adjacent the second flow passage to a side adjacent the first flow passage;
    (c) applying a pressure in the first flow passage sufficient to provide a bulk flux of the oxidant through the porous medium into the second chamber;
    (d) adjusting the flow of the alkane such that a ratio of diffusive flux of the alkane into the porous medium to the bulk flux of the oxidant through the porous medium is greater than 1:1;
    (e) contacting the oxidant and the alkane at the catalyst within the porous medium under reaction conditions sufficient to produce the olefin, which has twice the number of carbon atoms as the alkane, and which thereafter flows into the second flow passage and exits through an outlet in the second chamber.

2. The process of claim 1 wherein the alkane is a C1-4 alkane selected from methane, ethane, propane, n-butane, iso-butane, and mixtures thereof; and wherein the olefin is a C2-8 olefin having twice the number of carbon atoms as the C1-4 alkane.

3. The process of claim 1 wherein the oxidant comprises an oxidizer selected from oxygen, sulfur vapor, hydrogen sulfide and methylsulfide; and wherein the oxidant further comprises a diluent selected from nitrogen, carbon dioxide, inert gases, and mixtures thereof.

4. The process of claim 1 wherein the oxidant comprises an oxidizer and wherein a molar ratio of alkane to oxidizer fed to the process is greater than 1.9:1 and less than 5:1.

5. The process of claim 1 wherein the porous medium comprises a porous ceramic material selected from the group consisting of porous aluminas, silicas, aluminosilicates, titanium oxides, zirconium oxides, mullite, hexaluminates, and spinels, anyone of which is optionally modified with one or more alkali or alkaline elements; or wherein the porous medium comprises a porous metallic material selected from stainless steel, iron-chromium-aluminum alloys and nickel-chromium-aluminum alloys.

6. The process of claim 1 wherein the porous medium comprises a plurality of pores, channels, cavities, or void spaces, which have an average diameter or critical cross-sectional dimension ranging from 2 microns (2 μm) to 100 μm.

7. The process of claim 1 wherein the porous medium has a porosity of at least about 30 percent and less than about 90 percent.

8. The process of claim 1 wherein the oxidative coupling catalyst is selected from the group consisting of compounds of magnesium, manganese, sodium tungstate, and silica (Na/Mg/W/Mn/SiO$_2$), lithium magnesium oxide (Li/MgO), lanthanum oxide (La$_2$O$_3$), strontium-magnesium-calcium-doped lanthanum oxide (Sr,Mg,Ca/La$_2$O$_3$), acid or sodium modified ZSM-5 (H/Na-ZSM-5), and rhenium, gallium, tungsten, and/or molybdenum modified ZSM-5 and MCM-22.

9. The process of claim 1 wherein the ratio of diffusive flux of the alkane into the porous medium to the bulk flux of the oxidant through the porous medium (DF$_{ALK}$:BF$_{OX}$) is greater 10:1 and less than 100:1.

10. The process of claim 1 wherein the process is conducted at a temperature greater than 500° C. and less than 900° C.

11. The process of claim 1 wherein the process is conducted at an overall process pressure of greater than 0.69 kPa and less than 3,447 kPa as measured at the outlet of the second chamber; while a pressure at the inlet to the first chamber is at least +13.8 kPa to +35 kPa greater than the overall process pressure.

12. The process of claim 1 wherein the process is conducted at an alkane flow rate greater than about 0.05 g/g-cat/hr and less than about 240 g/g-cat/hr, and at an oxidant flow rate greater than 0.2 g/g-cat/hr and less than about 40 g/g-cat/hr, wherein the oxidant flow rate is the total flow rate of an oxidizer and a diluent.

13. The process of claim 1 wherein a flow of air is fed through the first inlet into the first chamber; and wherein a flow of methane is fed into the second inlet into the second chamber; and wherein the oxidative coupling product produced is ethylene.

* * * * *